United States Patent [19]

Wick

[11] 4,314,063

[45] Feb. 2, 1982

[54] 1-ETHYL-1,4,5,6-TETRAHYDRO-6-(2-NAPHTHYL)-4-OXO-NICOTINIC ACID AND LOWER ALKYL ESTERS THEREOF

[75] Inventor: Alexander E. Wick, Le Mesnil-le Roy, France

[73] Assignee: Hoffmann-La Roche Inc., Nutley, N.J.

[21] Appl. No.: 235,870

[22] Filed: Feb. 19, 1981

Related U.S. Application Data

[62] Division of Ser. No. 166,506, Jul. 7, 1980, Pat. No. 4,278,798.

[51] Int. Cl.$^3$ ............................................. C07D 213/55
[52] U.S. Cl. ...................................... 546/298; 560/38; 562/443
[58] Field of Search ........................................ 546/298

[56] References Cited

U.S. PATENT DOCUMENTS

4,220,648 9/1980 Youngdale ........................ 546/298

*Primary Examiner*—Alan L. Rotman
*Attorney, Agent, or Firm*—Jon S. Saxe; Bernard S. Leon; William G. Isgro

[57] ABSTRACT

1-Ethyl-1,4-dihydro-6-(2-naphthyl)-4-oxonicotinic acid and $C_{1-6}$-alkyl esters thereof as well as their alkali metal, alkaline earth metal or ammonium salts are described. The foregoing compounds are useful as central nervous system stimulants. Also described are 1-ethyl-6-(2-naphthyl)-4-oxo-1,4,5,6-tetrahydronicotinic acid and $C_{1-6}$-alkyl esters thereof, which are useful as intermediates.

3 Claims, No Drawings

1-ETHYL-1,4,5,6-TETRAHYDRO-6-(2-NAPHTHYL)-4-OXO-NICOTINIC ACID AND LOWER ALKYL ESTERS THEREOF

This is a division of application Ser. No. 166,506, filed July 7, 1980, now U.S. Pat. No. 4,278,798 issued July 14, 1981.

BRIEF SUMMARY OF THE INVENTION

The invention relates to 1-ethyl-1,4-dihydro-6-(2-naphthyl)-4-oxonicotinic acid and esters thereof of the formula

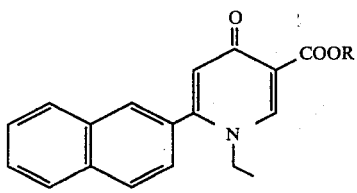

wherein R is hydrogen or $C_{1-6}$-alkyl, as well as alkali metal, alkaline earth metal and optionally substituted ammonium salts thereof.

In another aspect, the invention relates to 1,4,5,6-tetrahydronicotinic acid or an ester thereof of the formula

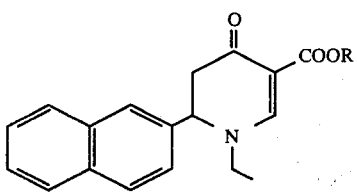

wherein R is hydrogen or $C_{1-6}$-alkyl, and the compound of the formula

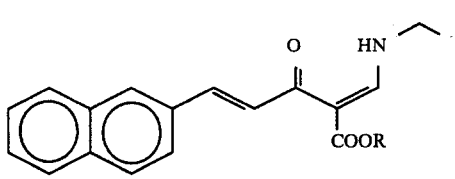

wherein R is hydrogen or $C_{1-6}$-alkyl, which are useful as intermediates.

In yet another aspect, the invention relates to a process for preparing the compounds of formula I.

DETAILED DESCRIPTION OF THE INVENTION

The invention relates to 1-ethyl-1,4-dihydro-6-(2-naphthyl)-4-oxonicotinic acid and esters thereof characterized by the formula

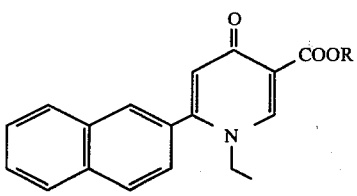

wherein R is hydrogen or $C_{1-6}$-alkyl, as well as alkali metal, alkaline earth metal and optionally substituted ammonium salts thereof.

As used herein, the $C_{1-6}$-alkyl residues denote straight- or branched-chain residues such as, for example, methyl, ethyl, propyl, isopropyl, tert.-butyl, or the like.

The compounds of the invention can be prepared from the corresponding 1,4,5,6-tetrahydronicotinic acid or ester thereof of the formula

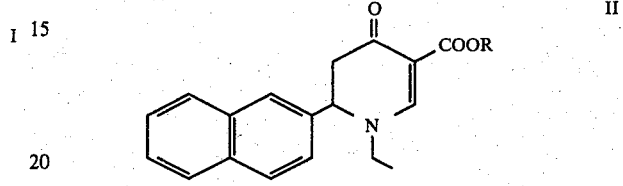

wherein R is as previously described, by dehydrogenation of the 5,6-position and, if desired, the acid obtained is converted into an alkali metal, alkaline earth metal or optionally substituted ammonium salt or the acid obtained is esterified with a $C_{1-6}$-alkanol, or a methyl ester obtained is saponified.

The dehydrogenation of a compound of formula II in accordance with the invention can be carried out utilizing known methods, conveniently with a substituted benzoquinone, such as 2,3-dichloro-5,6-dicyano-1,4-benzoquinone (DDQ) or tetrachloro-1,4-benzoquinone (chloranil), in an inert organic solvent, such as methylene chloride, benzene or dioxane, and at a temperature in the range of from room temperature to the reflux temperature of the reaction mixture. In general, one proceeds by adding a solution of the substituted benzoquinone dropwise to the solution of the tetrahydronicotinic acid derivative, whereby one can insure that equimolecular amounts are reacted. In the case of a colorless starting material the end of the reaction can be detected readily by the coloration of the reaction mixture which occurs. The reaction product can be isolated from the mixture in the usual manner and purified, for example, by recrystallization extractive or chromatographical procedures.

Not only the esterification of a compound I with R=hydrogen, which can be achieved under neutral conditions or, preferably, with an alkanol using acid catalysts, in a suitable solvent, but also conversion of the acid into a salt by reaction with a base as well as the saponification of an ester I to the corresponding acid is effected in a known manner. Exemplary of the bases that can be utilized to form salts are: potassium hydroxide, sodium hydroxide, calcium hydroxide, ammonium hydroxide, diethanolamine, and the like. Conversion of the ester to the corresponding acid can be effected by both acid or base catalysed reactions.

The starting compounds of formula II can be prepared from 2-naphthyl aldehyde in accordance with the Reaction Scheme which follows:

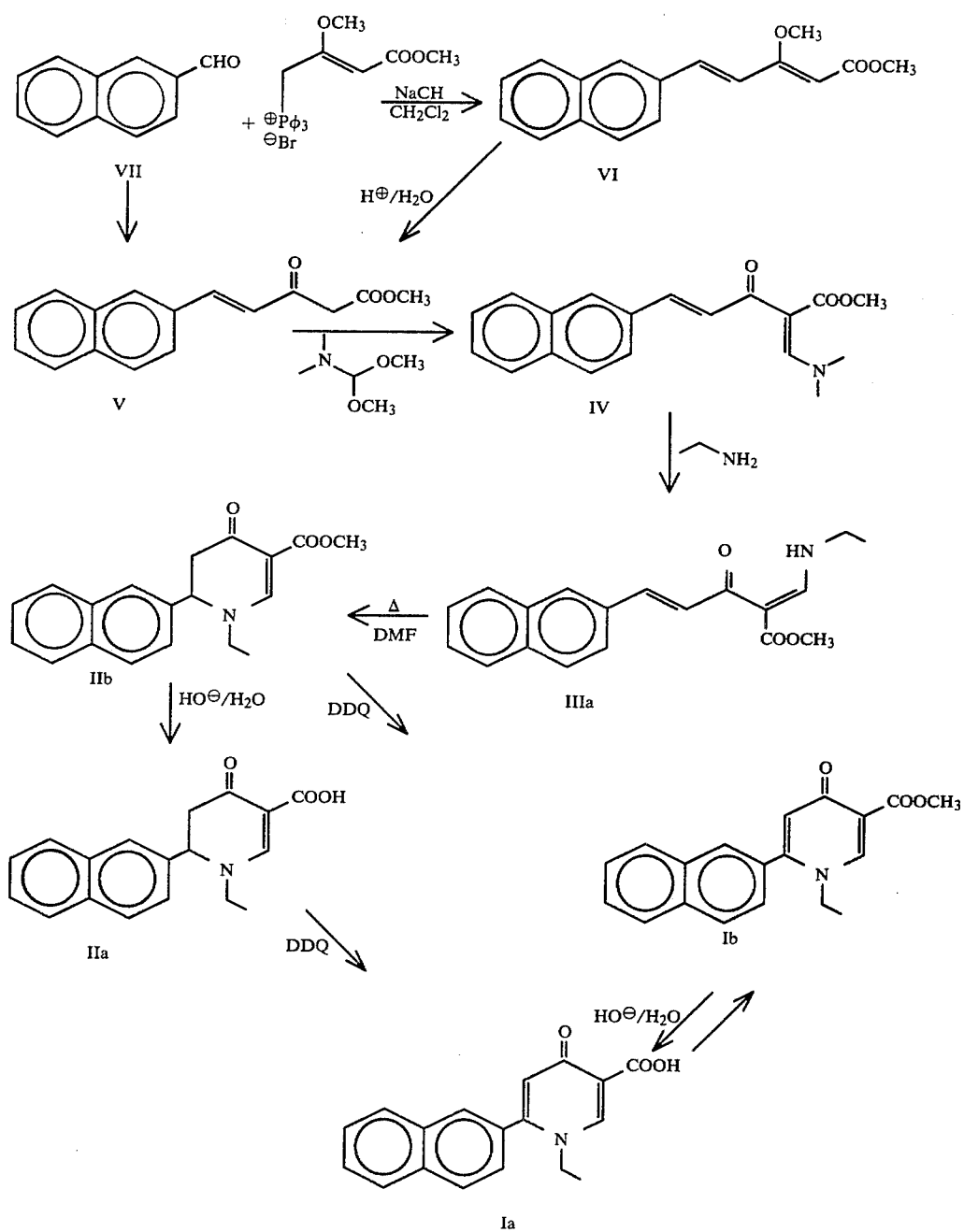

The intermediate products of formulas II and III are novel compounds and form part of the present invention.

The compounds of formula I are pharmacologically active. They possess, in particular, a stimulating action on the central nervous system, and are characterized by low acute toxicities. Thus, for example, 1-ethyl-1,4-dihydro-6-(2-naphthyl)-4-oxonicotinic acid is substantially superior to nomifensin (8-amino-1,2,3,4-tetrahydro-2-methyl-4-phenylisoquinoline, known to be useful as a thymoleptic and central nervous system stimulant) and has about the same $LD_{50}$. Furthermore, it stands out advantageously from d-amphetamine and d-methamphetamine in having about the same strength of action but substantially lower $LD_{50}$ (see Table I).

TABLE 1

| Compound | $LD_{50}$ [mg/kg] (mouse) | Turning rat test 1 minimum active dosage [mg/kg] i.p. |
|---|---|---|
| 1-Ethyl-1,4-dihydro-6-(2-naphthyl)-4-oxonicotinic acid | 170 p.o. | 1 |
| Nomifensin | 300–600 p.o. | 3 |
| d-Amphetamine . ½ $H_2SO_4$ | 35 p.o. 14 i.v. 22 s.c. | 1 |
| d-Methamphetamine . HCl | 9.5 i.v. 14 s.c. | 1 |

1 Arch. int. Pharmacodyn. Ther. 217, 118–130 (1975)

METHOD

Female rats weighing 150 g are anaesthetised with pentobarbital (50 mg kg$^{-1}$ i.p.) and fixed in a stereotaxic apparatus (David Kopf). A unilateral (right side) injection into the MFB (medial forebrain bundle) of 6-OHDA (6-hydroxy-dopamine), 3 µg as base, dissolved in 4 µl of Ringer solution containing 0.02% ascorbic acid, is carried out through a stainless-steel cannula (diameter 0.3 mm) connected to a microsyringe. The liquid is injected at a speed of 1 µl min$^{-1}$ by means of a high precision infusion pump. In order to reach the MFB (medial forebrain bundle), the following coordinates are used: A=+3.8 mm, L (right)=0.9 mm, V=−3 mm according to the Atlas of König and Klippel.

After 3 weeks recovery period, the operated rats are injected with apomorphine, 1 mg kg$^{1-}$ i.p. Those animals showing a regular contralateral (i.e., away from the lesioned side) turning, recorded automatically during 1 hour in a rotometer, are selected for further experiments. At least one week is allowed between each injection of screening compounds.

Drugs which induce rotation are dopamine receptor agonists. If the turning is contralateral (i.e., away from the lesioned side) the drugs are classified as "apomorphine-like", which indicates a direct dopamine-receptor stimulation (postsynaptic). The denervated striatum is more sensitive to dopamine receptor agonistes than the intact one. Agonists therefore affect the denervated striatum more than the intact one. This inbalance results in contralateral turning (rotation).

If the rotation is ipsilateral (i.e., towards the lesioned side), the drugs are classified as "amphetamine-like", which means that they release and/or block the reuptake of dopamine (presynaptic) from nerve terminals on the intact side, whereas they have little if any effect on the striatum with denervated dopamine neurons. The result of this inbalance is an ipsilateral turning.

The total number of ipsilateral or contralateral turns (full rotation around the vertical axes of the body) made by each rat, is automatically recorded over the time (usually 1 hour). 5 rats are injected for each dose and the mean of total turns per hour is determined.

A compound is said active, if it produces more than 100 turns/hour. If a drug induces rotation, but less than 100 turns/hour, it is indicated as slightly active. If no rotation takes place, the drug is considered inactive. The results are expressed as:

Minimal effective dose—if the drug is active
Highest dose tested—if the drug is inactive.

The compounds of formula I of the invention can be used for the stimulation of the central nervous system in the form of pharmaceutical preparations, with direct or delayed liberation of the active substance, in mixture with an organic or inorganic inert carrier material suitable for oral or parenteral application, for example, water, gelatin, gum arabic, lactose, starch, magnesium stearate, talc, vegetable oils, polyalkyleneglycols, and the like. The pharmaceutical preparations can be solid in form, for example, as tablets, dragees, suppositories, capsules; or in liquid form, for example, as solutions, suspensions or emulsions. If necessary, the pharmaceutical preparations can be sterilized and/or contain additional adjuvant substances, such as preserving, stabilizing, wetting or emulsifying agents, agents to improve flavor, salts for the variation of the osmotic pressure or buffer substances.

The pharmaceutical preparations can be prepared in the manner known in the art, for example, by mixing the active substance with a non-toxic, inert carrier material suitable for therapeutic administration and finishing the mixture obtained into the suitable galenic form.

The compounds of formula I of the invention can be administered in an amount which is in the range of from 100 µg to 10 mg/kg body weight, per day.

The Examples which follow further illustrate the invention. All temperatures are stated in degrees Centigrade, unless otherwise mentioned.

EXAMPLE 1

Preparation of 1-ethyl-1,4-dihydro-6-(2-naphthyl)-4-oxonicotinic acid

12 G. of methyl 2-[(ethylamino)-methylene]-5-(2-naphthyl)-3-oxo-4-pentenoate were dissolved in 100 ml. of dimethylformamide and stirred at 150° C. for 4 hours. After evaporation of the solvent under high vacuum at 60° C., there was obtained 12 g. of a dark red, viscous oil, which was dissolved in 60 ml. of toluene. The solution was heated to reflux and a suspension of 10.6 g. of chloranil in 50 ml. of toluene was allowed to drop in slowly. The reaction mixture obtained was treated with ethyl acetate and shaken out three times with ice-cold 3 N hydrochloric acid. The acid extracts were brought to pH 6 with 4 N sodium hydroxide while cooling and extracted three times with methylene chloride. The organic extracts were washed with saturated sodium chloride solution, dried over sodium sulfate and evaporated. There were obtained 10 g. of a brownish oil, which crystallized from ether/methanol and yielded 8.7 g. (73%) of 1-ethyl-1,4-dihydro-6-(2-naphthyl)-4-oxonicotinic acid methyl ester, mp 138°–139° C. (colorless crystals).

3.8 G. of 1-ethyl-1,4-dihydro-6-(2-naphthyl)-4-oxonicotinic acid methyl ester were dissolved in 10 ml. of methanol and treated with 20 ml. of 1 N sodium hydroxide. After 15 minutes stirring at room temperature, the reaction mixture was extracted two times with ethyl acetate and the aqueous phase was neutralized with 1 N hydrochloric acid while cooling. The free acid thereby precipitating was filtered off under suction, washed with cold water and ether and recrystallized from ethanol/methylene chloride. There was obtained 3.1 g. (85.5%) of 1-ethyl-1,4-dihydro-6-(2-naphthyl)-4-oxonicotinic acid in the form of colorless crystals, mp 209°–210° C.

The starting material was obtained in accordance with the following:

84 Ml. of 50% sodium hydroxide were added dropwise while stirring at room temperature to a solution of 25 g. of 1-naphthyl aldehyde and 78 g. of 2-methoxy-3-(methoxycarbonyl)-allyltriphenyl-phosphonium bromide in 300 ml. of methylene chloride. After 3 hours stirring at room temperature and 1 hours stirring at 40° C., the phases were separated. The aqueous phase was extracted two times with methylene chloride and the combined organic phases were washed neutral with water. After drying over sodium sulfate and evaporation of the solvent, there was obtained a viscous, light yellow oil, which crystallized to some extent. The mixture was digested with ether/ethyl acetate, evaporated and recrystallized from methanol. There were obtained 29.4 g. (68.5%) of methyl 3-methoxy-5-(2-naphthyl)-2,4-pentadienoate in the form of colorless crystals, mp 94°–96° C.

A solution of 23.5 g. of methyl 3-methoxy-5-(2-naphthyl)-2,4-pentadienoate in 500 ml. of methanol was treated with 50 ml. of concentrated hydrochloric acid. After about 3 minutes stirring at room temperature, there precipitated a white, crystalline product, which was filtered off, washed with cold water and dissolved in methylene chloride. The organic phase was shaken out two times with ice-cold, saturated sodium bicarbonate solution, dried over sodium sulfate and evaporated. After recrystallization of the crystalline residue from methanol, there were obtained 20.8 g. (93%) of methyl 5-(2-naphthyl)-3-oxo-4-pentenoate in the form of colorless crystals, mp 86°–87° C.

9 G. of methyl 5-(2-naphthyl)-3-oxo-4-pentenoate and 4.7 g. of dimethylformamide dimethylacetal were dissolved in 100 ml. of toluene and stirred at 60° C. for 22 hours. After cooling, the reaction mixture was evaporated. There were obtained about 10 g. of a dark red, viscous oil, which was treated with a solution of 100 g. of ethylamine in 1 l. of toluene. The reaction mixture was stirred at room temperature for 20 hours, evaporated and the crude product was purified by column chromatography [silica gel, methylene chloride/methanol (19:1, v/v)]. After recrystallization from ether/pentane, there were obtained 6.0 g. (55%) of methyl 2-[(ethylamino)-methylene]-5-(2-naphthyl)-3-oxo-4-pentenoate in the form of light yellowish crystals, mp 80°–82° C.

EXAMPLE 2

Tablets of 120 mg. or 500 mg. were prepared containing:

| | | |
|---|---|---|
| 1-Ethyl-1,4-dihydro-6-(2-naphthyl)-4-oxonicotinic acid | 10.0 mg. | 150 mg. |
| Maize starch | 50.0 mg. | 160 mg. |
| Lactose | 58.0 mg. | 180 mg. |
| Talc | 1.5 mg. | 7 mg. |
| Magnesium stearate | 0.5 mg. | 3 mg. |
| | 120.0 mg. | 500 mg. |

I claim:
1. A compound of the formula

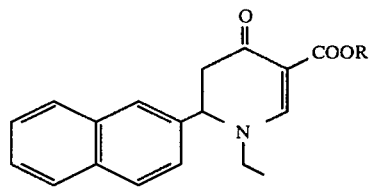

wherein R is hydrogen or $C_{1-6}$-alkyl.

2. A compound in accordance with claim 1, 1-ethyl-6-(2-naphthyl)-4-oxo-1,4,5,6-tetrahydronicotinic acid.

3. A compound in accordance with claim 1, 1-ethyl-6-(2-naphthyl)-4-oxo-1,4,5,6-tetrahydronicotinic acid methyl ester.

* * * * *